(12) United States Patent
Mathis et al.

(10) Patent No.: US 8,911,465 B2
(45) Date of Patent: Dec. 16, 2014

(54) DEVICES, SYSTEMS, METHODS AND KITS FOR PERFORMING SELECTIVE DISSECTION OF LUNG TISSUE

(75) Inventors: Mark Mathis, Fremont, CA (US); Amelia Lasser, Menlo Park, CA (US); David Lehrberg, Mountain View, CA (US)

(73) Assignee: PneumRx, Inc., Mountain View, CA (US)

( * ) Notice: Subject to any disclaimer, the term of this patent is extended or adjusted under 35 U.S.C. 154(b) by 872 days.

(21) Appl. No.: 11/839,640

(22) Filed: Aug. 16, 2007

(65) Prior Publication Data

US 2008/0045993 A1   Feb. 21, 2008

Related U.S. Application Data

(60) Provisional application No. 60/822,542, filed on Aug. 16, 2006.

(51) Int. Cl.
| | |
|---|---|
| *A61B 17/00* | (2006.01) |
| *A61B 19/00* | (2006.01) |
| *A61B 18/00* | (2006.01) |
| *A61B 17/32* | (2006.01) |
| *A61B 17/24* | (2006.01) |

(52) U.S. Cl.
CPC ..... *A61B 17/32002* (2013.01); *A61B 2019/481* (2013.01); *A61B 2018/00541* (2013.01); *A61B 2017/320004* (2013.01); *A61B 17/320068* (2013.01); *A61B 2017/320028* (2013.01); *A61B 2017/242* (2013.01)
USPC ........................... 606/190; 606/171; 606/180

(58) Field of Classification Search
USPC ............ 606/190, 169, 39, 45, 167, 170, 171; 128/898
See application file for complete search history.

(56) References Cited

U.S. PATENT DOCUMENTS

| | | | | |
|---|---|---|---|---|
| 5,201,752 | A | * 4/1993 | Brown et al. | 606/190 |
| 5,632,717 | A | 5/1997 | Yoon | |
| 5,665,100 | A | 9/1997 | Yoon | |
| 5,683,349 | A | * 11/1997 | Makower et al. | 600/214 |
| 5,695,510 | A | * 12/1997 | Hood | 606/169 |
| 5,846,244 | A | 12/1998 | Cripe | |
| 6,039,748 | A | 3/2000 | Savage et al. | |

(Continued)

FOREIGN PATENT DOCUMENTS

| | | |
|---|---|---|
| FR | 2 268 505 A1 | 11/1975 |
| GB | 873 938 A | 8/1961 |

OTHER PUBLICATIONS

United States Patent and Trademark Office International Search Report and Written Opinion, Aug. 15, 2008, pp. 1-11, PCT/US07/76095.

(Continued)

*Primary Examiner* — Kathleen Holwerda
*Assistant Examiner* — Sarah Simpson
(74) *Attorney, Agent, or Firm* — Kilpatrick Townsend and Stockton LLP

(57) ABSTRACT

This invention relates to device, systems, kits and methods that enable selective dissection of lung tissue to remove diseased tissue from healthy tissue without damaging blood vessels or airways. The invention and methods enable minimally invasive lung surgery procedures by providing a device and method to perform automated dissection that discriminates against traumatizing critical lung tissue.

20 Claims, 10 Drawing Sheets

(56) References Cited

U.S. PATENT DOCUMENTS

| | | | |
|---|---|---|---|
| 6,454,781 B1 * | 9/2002 | Witt et al. | 606/169 |
| 6,770,070 B1 * | 8/2004 | Balbierz | 606/41 |
| 7,390,330 B2 | 6/2008 | Harp | |
| 2002/0069884 A1 * | 6/2002 | Boyd et al. | 128/898 |
| 2005/0177184 A1 * | 8/2005 | Easley | 606/167 |
| 2005/0216055 A1 * | 9/2005 | Scirica et al. | 606/219 |

OTHER PUBLICATIONS

Supplementary European Search Report of European Patent Application No. 07814166.0, mailed Aug. 31, 2010, 7 pages total.

* cited by examiner

DEVICES, SYSTEMS, METHODS AND KITS FOR PERFORMING SELECTIVE DISSECTION OF LUNG TISSUE

CROSS-REFERENCE

This application claims the benefit of U.S. Provisional Application No. 60/822,542 filed Aug. 16, 2006, entitled System and Method for Performing Selective Dissection of Lung Tissue which is incorporated herein by reference in its entirety.

FIELD OF THE INVENTION

The invention is directed to devices, methods, systems and kits that enable dissection of lung tissue in a fast and safe manner. In particular, it relates to an invention and methods that enable minimally invasive and selective dissection of tissue to remove diseased tissue from healthy tissue without damaging blood vessels or airways.

BACKGROUND OF THE INVENTION

The present invention relates to devices, methods, systems and kits that enable selective dissection of lung tissue to remove diseased tissue from healthy tissue without damaging blood vessels or airways. The invention and methods enable minimally invasive lung surgery procedures by providing a device and method to perform automated dissection that discriminates against traumatizing critical lung tissue.

Relatively few thoracic procedures are performed using minimally invasive or video assisted thoracic surgical techniques (VATS) even though they are well known to provide benefit to the patient by minimizing trauma and speeding recovery compared to open chest procedures. This is due, at least in part, to the fact that there are only a few available instruments designed specifically to enable thoracic procedures in this way.

Current clinical practice to remove lungs, lung lobes or lung tissue segments involve opening the chest by cutting the sternum or by spreading the ribs. Many times ribs are broken and often segments are surgically removed during these procedures. The orthopedic trauma alone presents considerable pain and it can complicate the recovery process with patients. Thoracic pain of this magnitude complicates the task of recovering a patient from general anesthesia since the body acclimates to forced ventilation and the pain can interrupt natural chest rhythm. Patients benefit dramatically from procedures that are performed through small incisions or ports in the chest without causing this orthopedic trauma.

The bulk of the procedural time and effort required to surgically remove lung tissue entails dissection of tissue away from critical structures such as arteries, veins and airways so they can be closed off properly and then transected. Currently, surgeons use standard forceps, scissors, and scalpel instruments to tease tissue away from these structures. This work is dangerous because the vasculature is coupled directly to the heart and a mistakenly lacerated vessel results in large, and sometimes, uncontrollable hemorrhage.

Dissection using manual instruments is slow because the physician must constantly anticipate stressing a critical structure and possibly rupturing the tissue. A typical technique involves plunging a scissor type instrument forward and then spreading it to tear tissue apart. It is slow, dangerous and requires good visualization and surgical skill to avoid complications.

Hence, there is a need for a device that is automated and safer and allows the physician to concentrate less on each stroke of a manual instrument and allows for a more minimally invasive approach.

SUMMARY OF THE INVENTION

The present invention provides a system, device and methods to perform selective tissue dissection.

The system includes a port or small hole-making instrument to deliver the invention through a small entry site in the chest to minimize orthopedic trauma.

In another embodiment, the system includes the invention and a scope instrument to enable the procedure to be performed minimally invasively. Open chest procedures may be performed through openings larger than 10 inches wide. However, the invention can be practiced through openings that are less than 10 inches across.

The invention is configured in a way that very small bits of tissue are dissected with each stroke of the device. The dissecting element may be grooved with, for example, a maximum groove width that is only opened to allow for the entry of tissue that is less than 5 mm, less than 3 mm, smaller than 1 mm or less than 0.5 mm and this would make it difficult for airways or critical veins or arteries to advance into a cutting area on the dissector element. For purposes of analogy in understanding the operation of the device of the invention, the device of the invention performs analogously to a hair shaver that is adapted to prevent cutting structures larger than a target size, such as tubular structures that are 0.5 mm in diameter or larger.

In a configuration of the dissector element or housing is configured is such that all sharp edges are configured within the groove feature. In some embodiments, some or all edges external to the grooves are dull although they may be tapered to enhance blunt dissection properties. Some features may be sharpened on the inside of the groove or outside, or both, in order to snag tissue to allow the reciprocating motion to stress the tissue to pull it apart, cut or dissect.

The size of the dissection action with each stroke is reduced to make the dissection perform safely but slowly. To enhance the speed of dissection, the invention should be driven by a work energy source that could include a motor driven by battery power, direct current, alternating current, air pressure, vacuum, electromotive induction or other means to cause linear or rotary motion. The rate of motion of the dissecting element can, for example, be dictated by the coupled mechanism that is driven by the motor. Typically, the dissecting element or elements is driven faster than, for example, 1 hertz. A rate higher than 10 hertz can also be used, as well as a rate more than 30 hertz or more than 50 hertz.

In an embodiment, the invention is configured long and thin so that it can fit through small holes in the chest. The effective length or reach of the device in an embodiment would be longer than 50 mm with a diameter less than 75 millimeters (mm). The diameter could be less than 25 mm but less than 20 mm.

The components of the invention be made of plastics, metals or both. The motor must be controllable by the physician at any time by way of actuating a switch or valve in line between the work energy source and the power source that drives the work source.

The physician can control the tilt or orientation of the dissecting element as the procedure progresses. In a configuration a mechanism may allow the physician to push a knob to control a mechanism that tilts or rotates or translates the dissector section of the invention from side to side. This will allow the physician to enter the chest from a single port or hole in the chest and maneuver the invention to the tissue in a multitude of trajectories.

In a method embodiment, a lobectomy surgery is performed using the invention to make dissections to separate adjacent pleura to complete the fissures between the lobe that is to be removed and adjacent lobes. The method includes the step of locating large airways, arteries and veins larger than approximately 0.5 mm or larger in diameter (e.g. generically referred to as structures) and carefully dissecting out of the lung tissue and/or tumors so they can be reliably clipped, stapled or sealed off with glue or other methods. As will be appreciated by those of skill in the art, failure to identify the critical structures in the lung may result in accidental laceration when the lobe is completely cut away from the adjacent lungs. Laceration or any procedure that allows for rupture of the arteries in this region greatly increases the risk of patient death since they transport the majority of the human cardiac output. Laceration could cause an immediate and uncontrollable hemorrhage that could result in patient death.

An additional method is directed to performing a lobectomy of a lung which comprises providing a surgical instrument with a source of work energy that is coupled to a dissecting member extending from the forward portion of the instrument; activating the source to induce motion of the dissecting member; contacting the dissecting member to adjacent pleurae along a fissure; and dissecting a lobe of lung away from a tubular lung structure. Additionally, the method can include visualizing the lung with an optical instrument, such as an endoscope. Tubular lung structure suitable for dissection include, but are not limited to bronchi, dissectible airways, veins and arteries. In some instances it may be desirable to adjust the projection of the dissection member into different trajectories.

An additional aspect is directed to a kit for removing a portion of a lung from structures of the lung. The kits comprises: a surgical instrument comprising an elongated housing having a longitudinal axis, a forward portion and a rearward portion of the housing, and a dissecting member extending from the forward portion of the housing; and a hole-making instrument for making an entry site to access a target lung section for the surgical instrument. The surgical instrument can be any suitable surgical instrument adapted and configured to remove a portion of a lung from structures of the lung. Additionally, the kit can be configured to include a variety of other components, including, for example, an optical instrument for communicating a visual of a target of the surgical instrument, such as an endoscope.

Incorporation by Reference

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
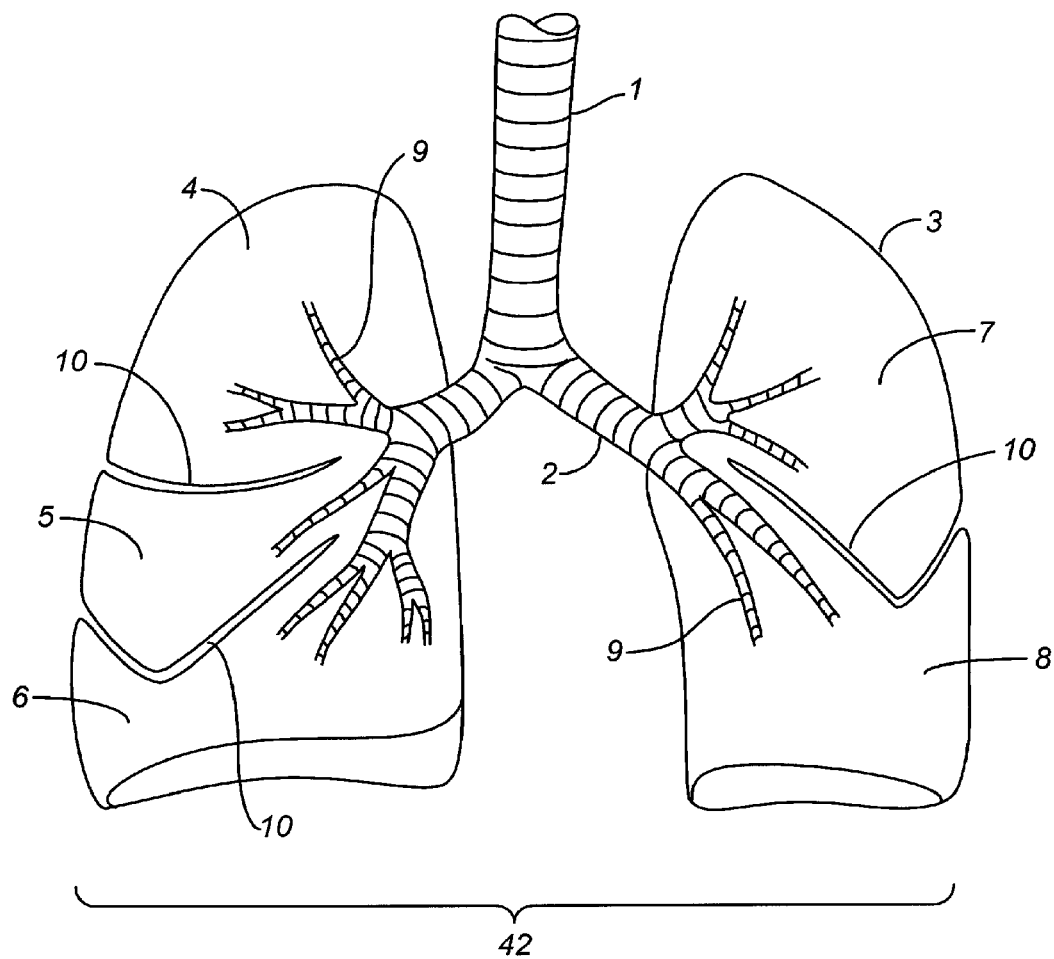
FIG. 1 illustrates an anterior view of the human lungs and bronchi tree.

FIG. 1 illustrates an anterior view of the human lung 42 and trachea 1. The trachea extends into the chest cavity to bifurcate into the primary bronchi 2 to then branch into the lung lobes and become bronchioles and small airways 9. The lungs are divided by fissures 10 that are lined with a membrane called the visceral pleura 3. The left side of the human chest contains the superior lobe 7 and the inferior lobe 8. The right side of the human chest contains the inferior lobe 4, the middle lobe 5 and the inferior lobe 6.

Figure 2:
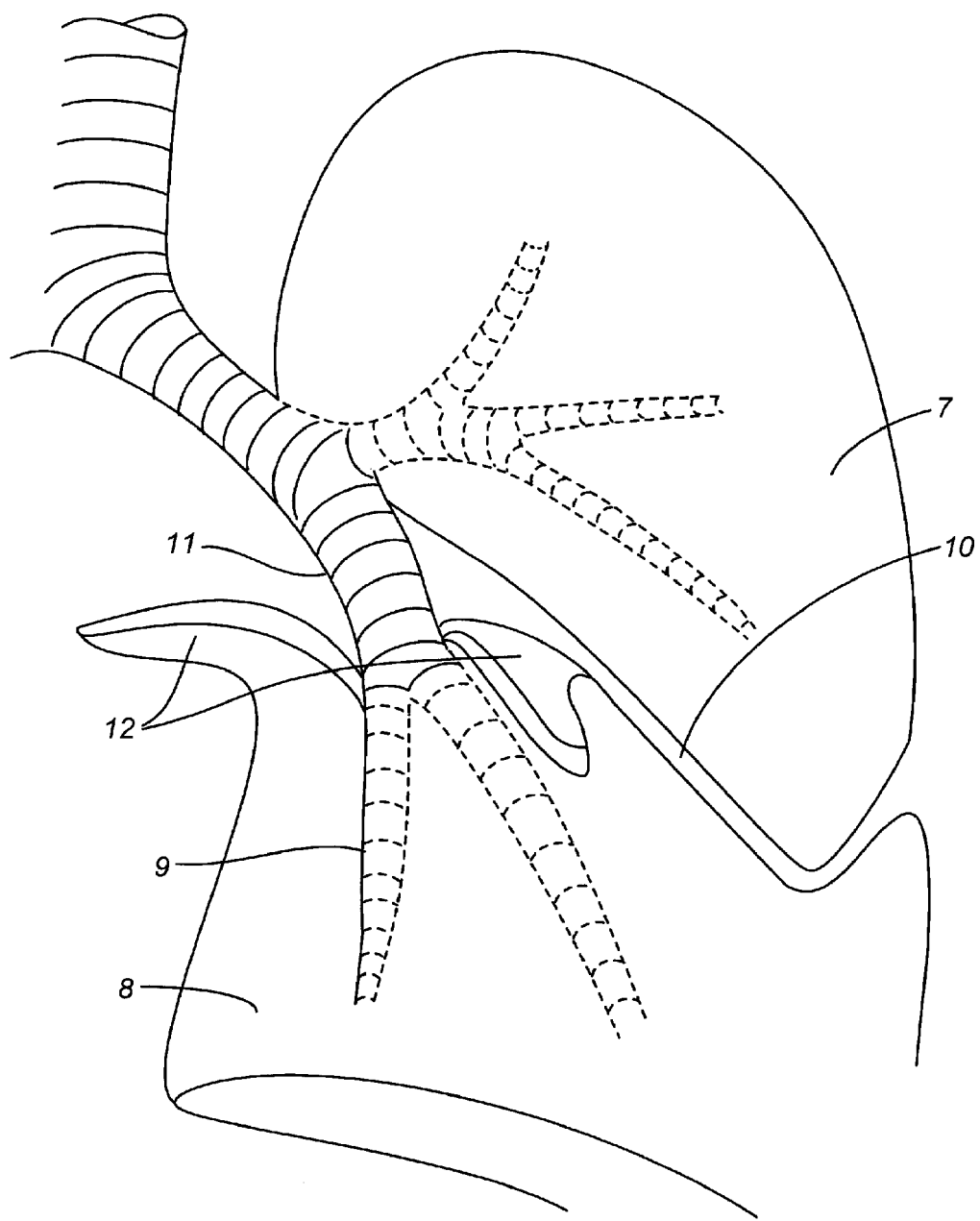
FIG. 2 illustrates an anterior view of the left lung to illustrate where the lobes are separated during a typical lobectomy surgery. Tissue is dissected away from the primary bronchus.

FIG. 2 illustrates the left side of the human chest cavity with the superior lobe 7 and inferior lobe 8, fissures 10, tissue that has been dissected away from the primary bronchi 12 where the surgeon will close off the bronchi and cut the lobe away 11. Lung tissue 12 must be dissected away from tubular Structures in the lung to access completely around these Structures to apply a closing or blocking device. The tissue 12 is dissected completely around the Structure approximately 25 mm down the length of the Structure. The cleared segment is typically longer than 10 mm. Sections longer than 5 mm or longer than 3 mm are also suitable alternatives.

Figure 3:
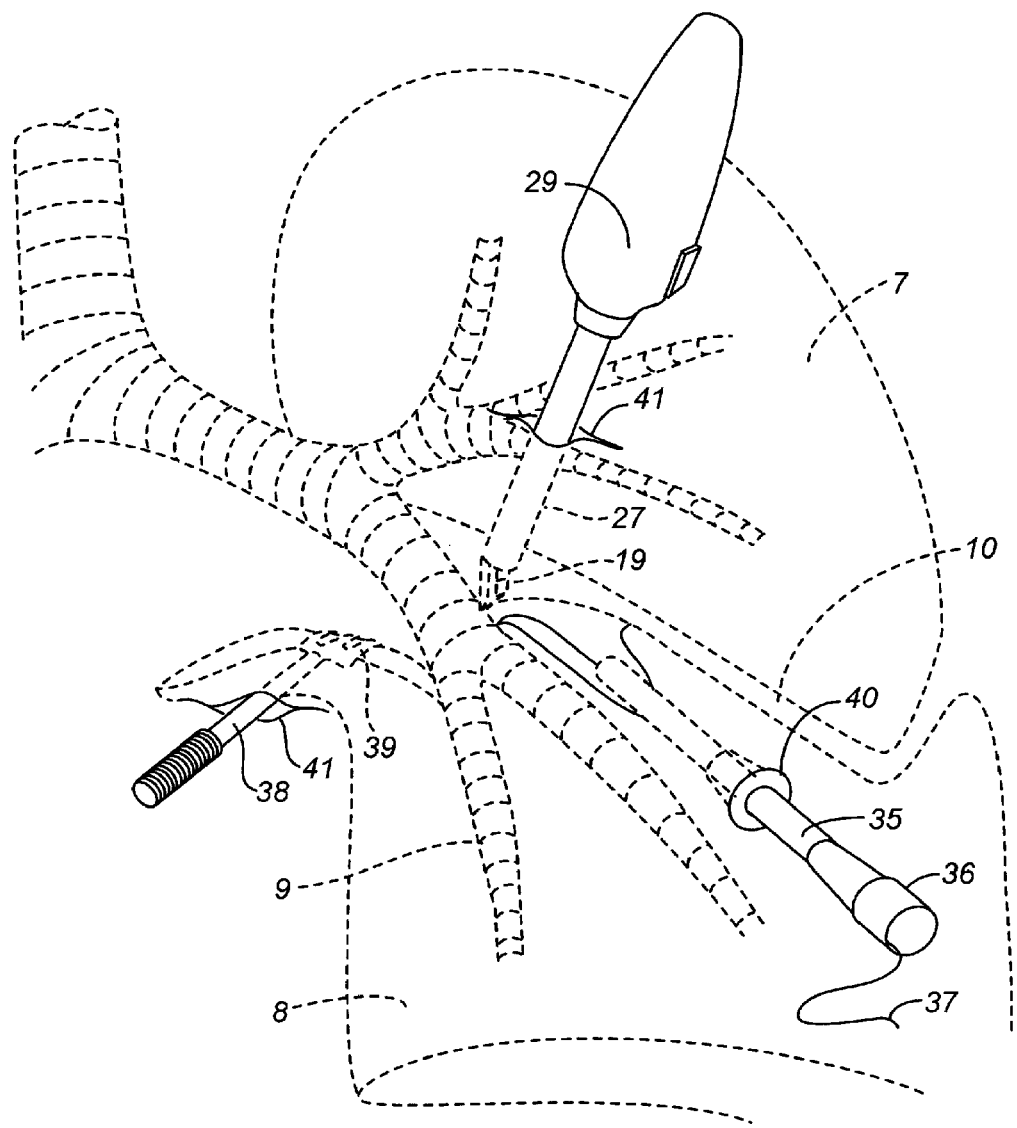
FIG. 3 illustrates the relative position of surgical instruments that are used for video assisted thoracic surgery (VATS) with the invention making the dissection of the tissue at the primary bronchi.

FIG. 3 illustrates a device 29 in use, engaging a dissecting member 19 to remove lung parenchyma away from bronchi 9. The other instruments are shown to present a typical video assisted thoracic surgery (VATS) system and how it would be used to perform a minimally invasive lobectomy. The device 29 is inserted through a small hole in the chest 41. Tissue is tensioned using a tensioning device 38 with teeth 39 that engage dissected tissue. An optical element 35 is inserted through a port 40 to communicate a visual image of the procedure to the camera 36 and to a monitor via a video cable 37. The figure further illustrates how the device dissects to separate the superior lobe 7 from the inferior lobe 8 so that the inferior lobe can be removed. The dissection that is shown must be performed on all airways, arteries and veins that communicate through or into the lobe that is being treated. The illustrated devices and methods are applicable for dissecting tissue from any of the aforementioned Structures. The invention can be equally useful for any surgical procedure in the thoracic cavity such as adhesion cutting, pneumonectomy, lobe segment removal, lung volume reduction surgery and other procedures to eliminate spontaneous pneumothorax, tumor removal, and general lung repair. The invention can be utilized in open surgery or introduced through a port or small hole in the chest.

Figure 4:
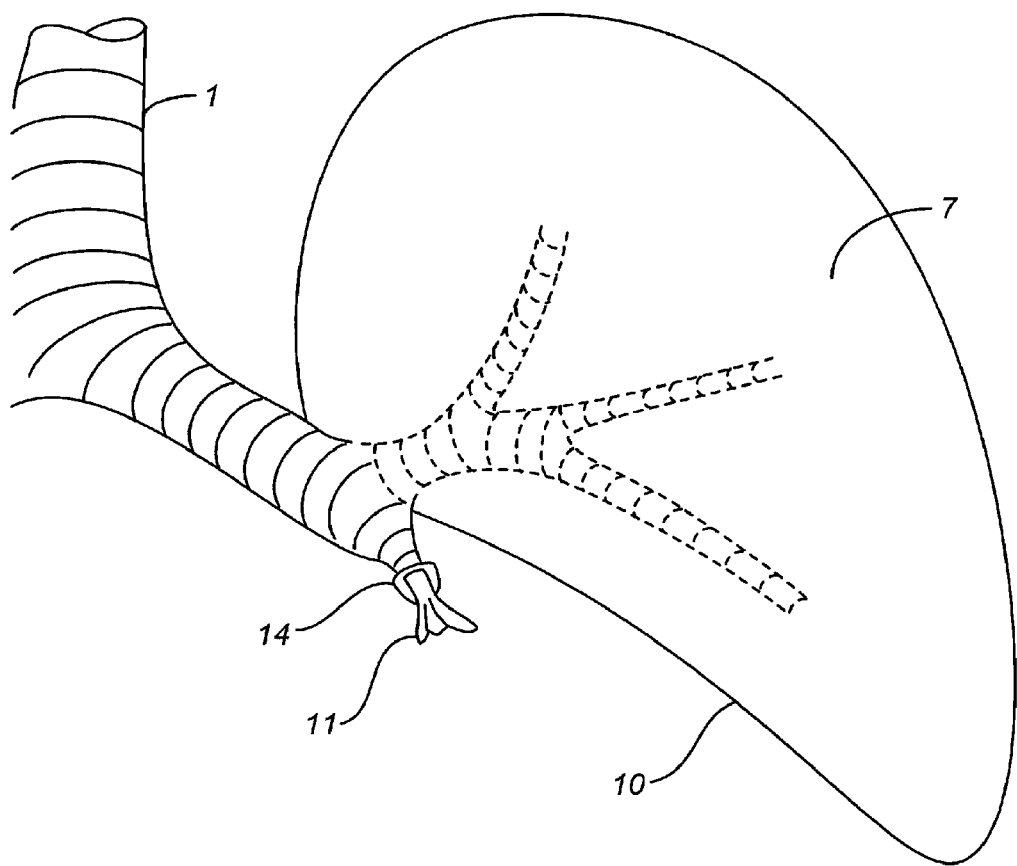
FIG. 4 illustrates the primary bronchus after it has been stapled or clipped and the lower lobe has been removed.

FIG. 4 is an anterior view of a chest cavity wherein the bronchi branch 11 that led to the inferior lobe is clipped 14 to occlude the branch and the lobe has been removed to leave only the superior lobe 7 in the chest.

Figure 5:
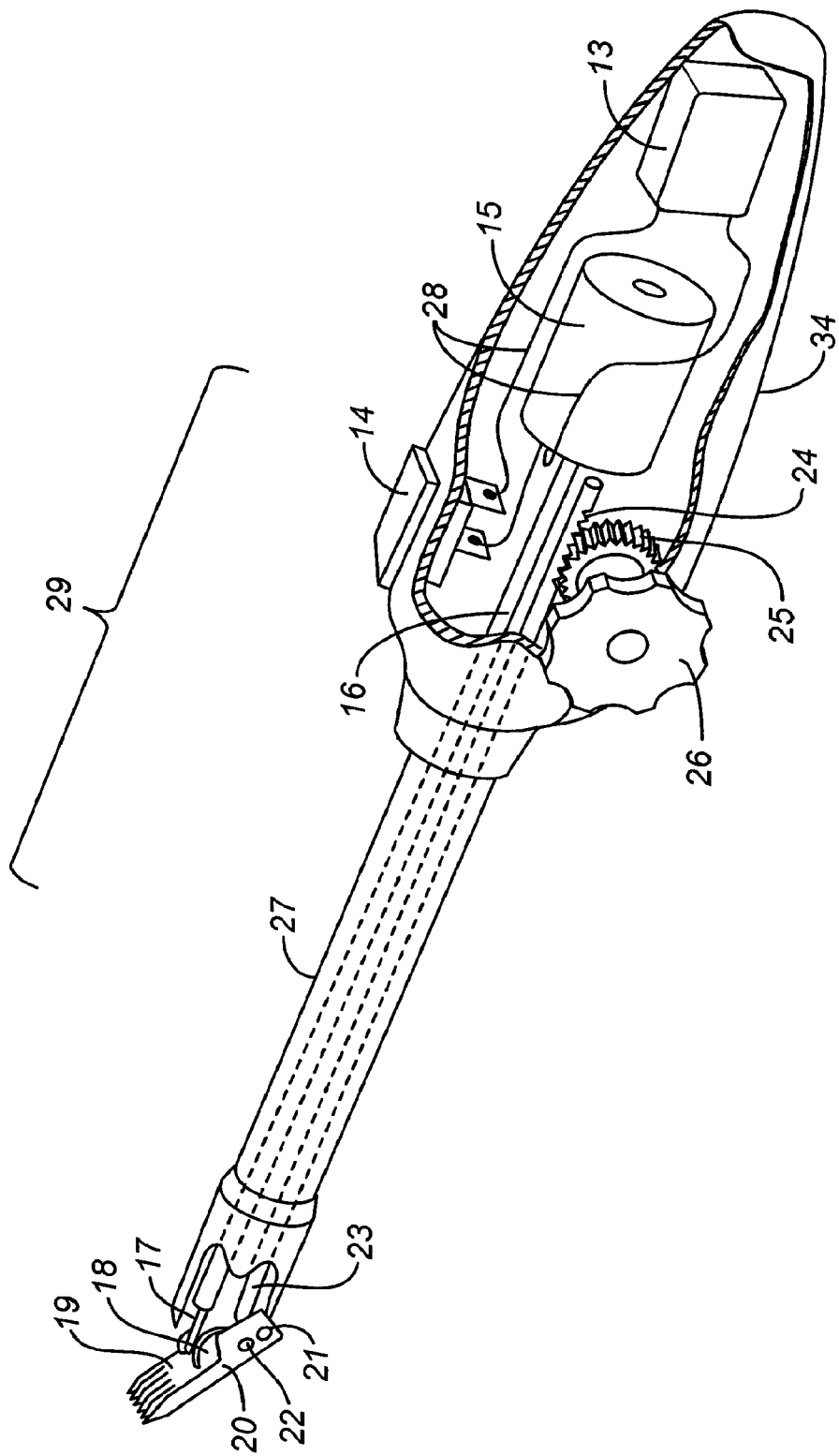
FIG. 5 illustrates the invention and main components in a cut away view.

FIG. 5 illustrates a cut away view of one configuration of the invention. The surgical system 29 operates by delivering work energy to a distal dissecting element to selectively dissect tissue away from specifically targeted lung tissue that must be preserved. The user can deliver work energy manually or control, via a switch 14, electrical current from a wall outlet or battery 13 to a motor 15 by way of wires 28 in the invention. The motor rotates the drive shaft 16 that is coupled to an eccentric cam 17 that intermittently loads the follower plates 18 to move the dissecting element 19 from side to side in a reciprocating manor. One or more dissector elements may be driven in a synchronized way or they may be driven in opposing directions to provide shear force on the lung tissue. The dissecting elements may be made of metal, plastic, ceramic or other dimensionally stable materials. The dissector element edge may be made of or coated with an abrasive material to enhance dissecting speed and efficiency. Coatings may be selected from the group of materials including plated, electroplated, sputtered, or vapor deposited metals, ceramics, glasses, plastics, fibrous materials such as carbon, oxides or other know substances that are used to provide abrasive surfaces. The dissecting element is guided by a dissector housing 20 that pivots about pin 21 and is stabilized and controlled by a pull rod 23 that is coupled to the dissector housing via coupler pin 22. The dissector housing may be adapted to hold tissue from moving to maximize the relative motion between tissue and the dissecting elements. Grooved tooth profiles are shown that enable fixation. The pull rod 23 incorporates a toothed rack 24 that engages a toothed gear 25 that is coupled to control knob 26. Rotation of the control knob adjusts the pivot angle of the dissecting system. The entire mechanism is housed in housing 34. The cutting mechanism may be detachable to be replaced with new cutters, or blades of different dimensions for different tasks during the procedure.

The power source can be selected from the group of 110 or 220 volt alternating current power or any direct current voltage that can be produced from a battery system such as Nickel Cadmium (NiCd), Nickel Metal Hydride (NiMH), Lithium Ion (LiON) or Smart batteries that have internal microprocessor circuits which help manage battery energy, report the state of the charge, predict running time or track battery usage. The mechanical parts of the invention can be made from metals, plastics, ceramics or a combination of these. The motor may comprise a gear reduction component or be coupled to one. A stop lock may be coupled to the pivot control mechanism. The motor may be a source for ultrasonic energy to drive the dissecting element at high frequencies above 10,000 hertz. A motor and gear reduction may slow the rotational speed to 10 hertz or less to enable slow dissection and physician feedback throughout the process. Any speed between the two would be ideal.

The invention shown in FIG. 5 illustrates a mechanism that can perform dissection by way of a moving dissector element using reciprocal motion. Another embodiment is a system that drives a rotary dissector element whereby the tooth spacing of the dissecting element or the dissecting housing accomplishes the same result as the reciprocating dissecting element.

Figure 6:
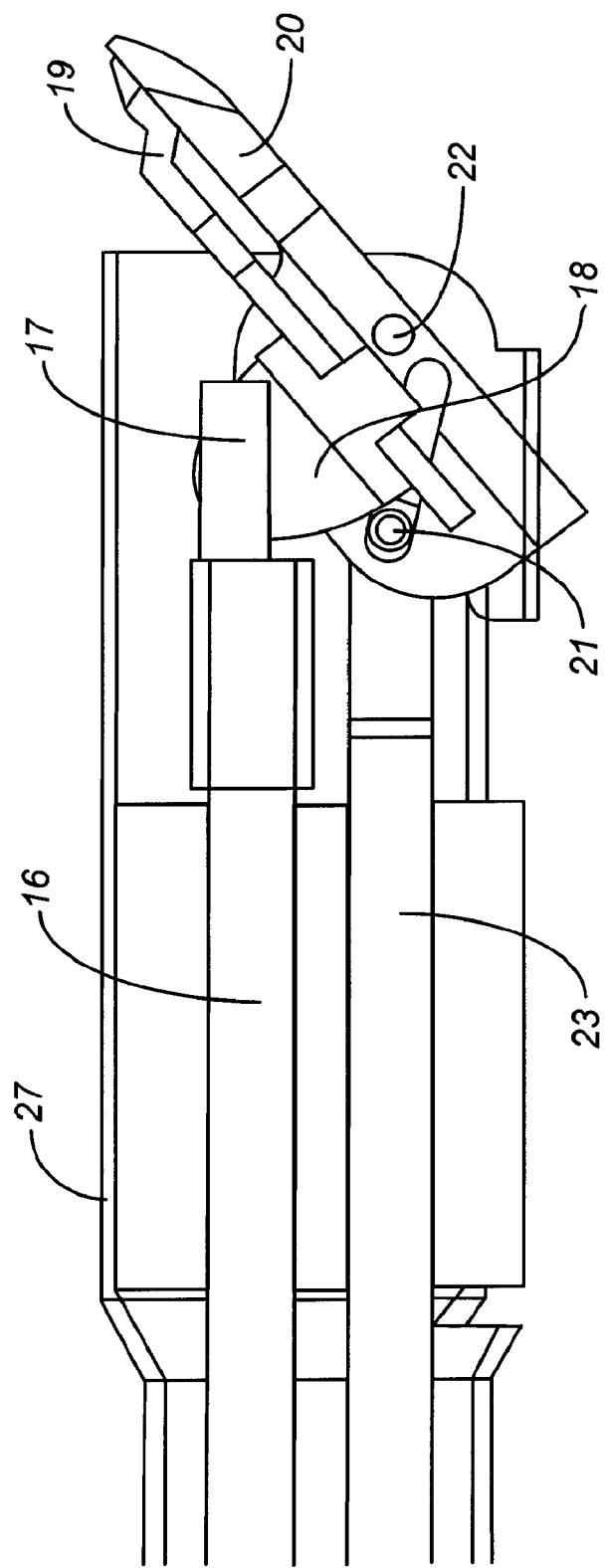
FIG. 6 is a detailed drawing of the working distal end of the invention.

FIG. 6 is a detailed view of the pivot mechanism showing the housing 27, drive shaft 16, cam 17, follower plate 18, dissecting element 19, dissector housing 20, coupler pin 22, pin 21 and pull rod 23. The pivot mechanism allows for the physician to controllably change the trajectory that the dissector operates. By manipulating this control, the physician can adjust the relative angle between the dissector element and the tissue or Structure that is being trimmed. Adjustment such as this allows the invention to be inserted into small ports or various locations between ribs with a high level of success to locate the point of dissection with a favorable angle of attack. The dissector can also be adjusted to one side or the other in the axis that the reciprocal motion takes place. This would be into or out of the plane of the illustration.

Figure 7:
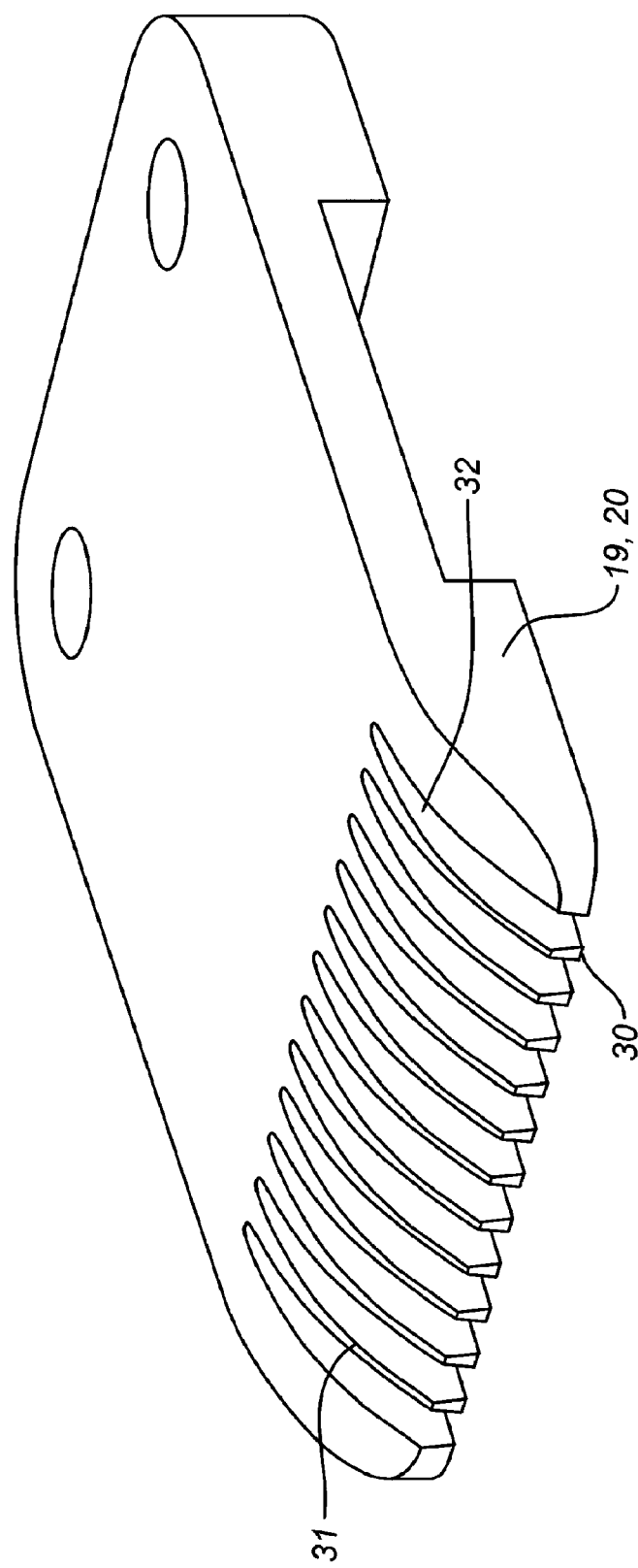
FIG. 7 is an isometric view of a dissecting element or dissecting housing.

FIG. 7 illustrates a configuration of a dissecting element 19 or dissector housing 20 that features grooved teeth 32 to engage tissue. The teeth are made with a tapered profile 31 and can be sharp at the extreme tips or faceted 30 to eliminate the possibility of cutting into a tubular Structure in the lung.

Figure 8:
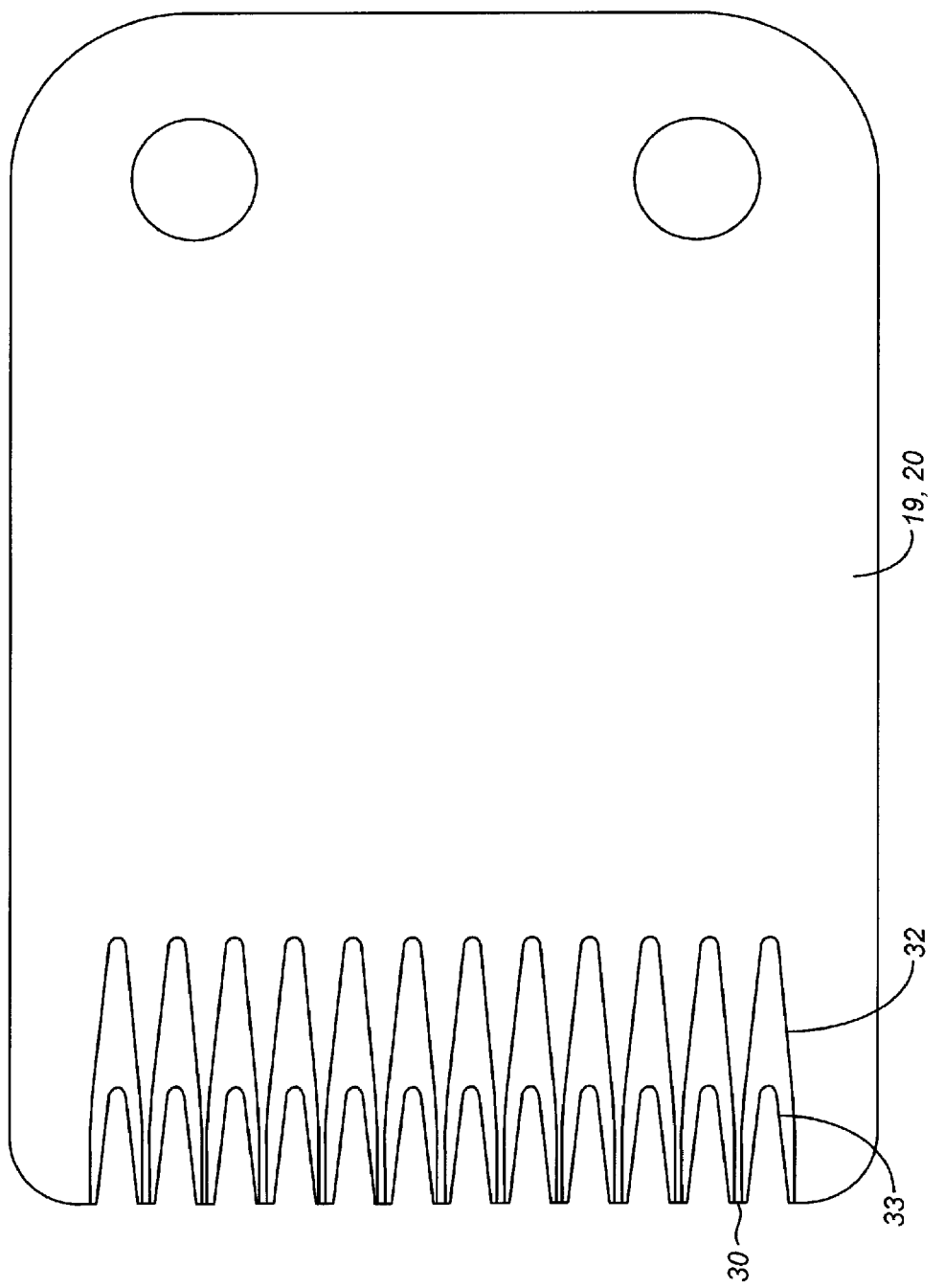
FIG. 8 is a top view of a dissecting element or dissecting housing.

FIG. 8 shows a top view of a dissecting element 19 or a dissector housing 20 that features grooved teeth 32 with facets 30 and sharpened blade sections 33 only on the inside of each groove. This ensures that cutting is performed only on tissue that is allowed inside the tooth groove. The width of the groove dictates the size of Structure that can be advanced into the cutting groove. The groove spacing can be the spacing from the start of one tooth to the start of the adjacent tooth. Typically the groove spacing is less than 5.0 mm, less than 3.0 mm, less than 1.0 mm, or less than 0.5 mm.

Figure 9:
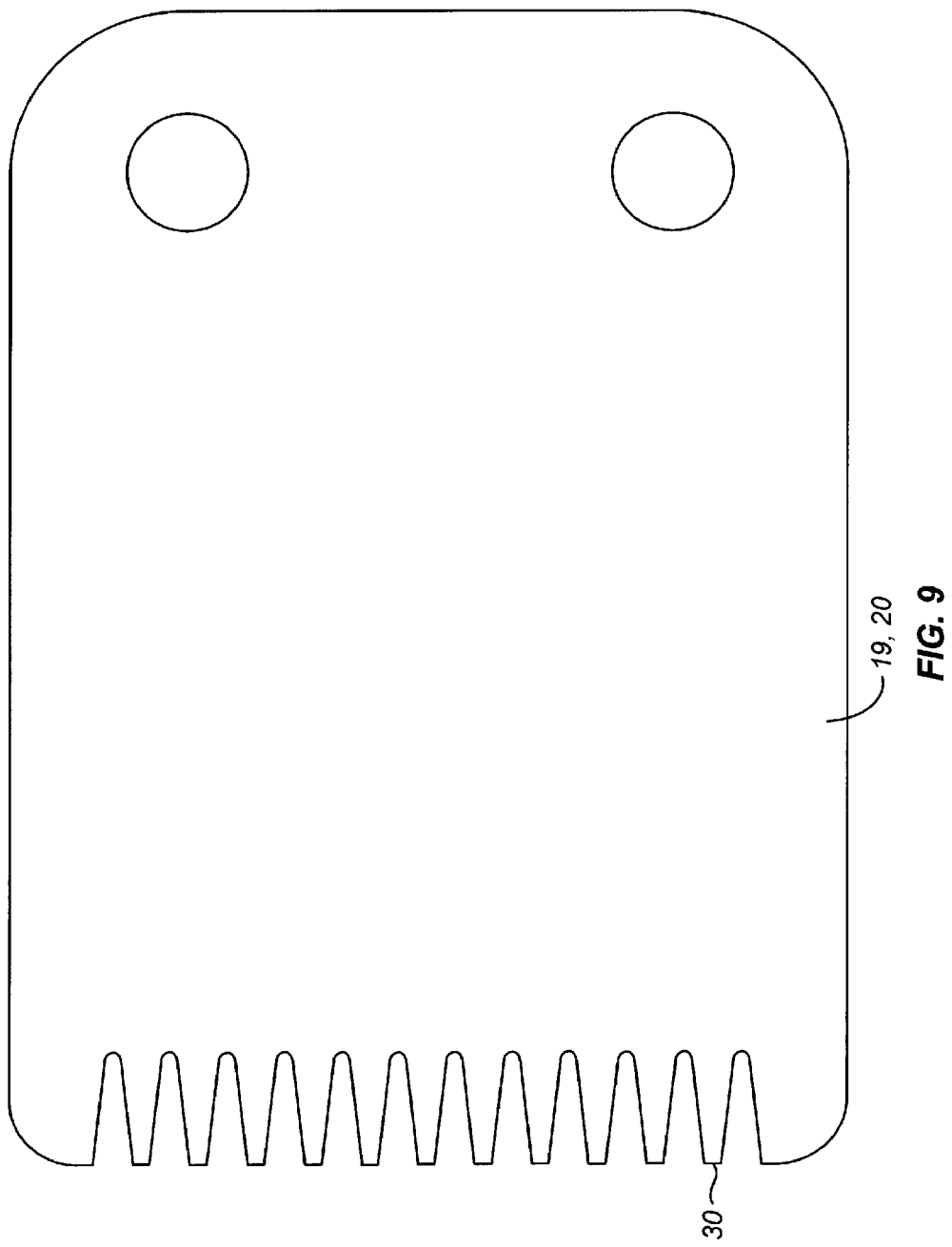
FIG. 9 is a top view of an alternative dissecting element or dissecting housing.

FIG. 9 illustrates a top view of a dissecting element 19 or a dissector housing 20 that features no cutting blade edges. This configuration is intended to engage tissue without cutting. The relative motion between the dissector element and the dissector housing will pulls apart soft lung tissue without cutting into critical Structures such as the arteries, veins, bronchi or dissectible airways.

Figure 10:
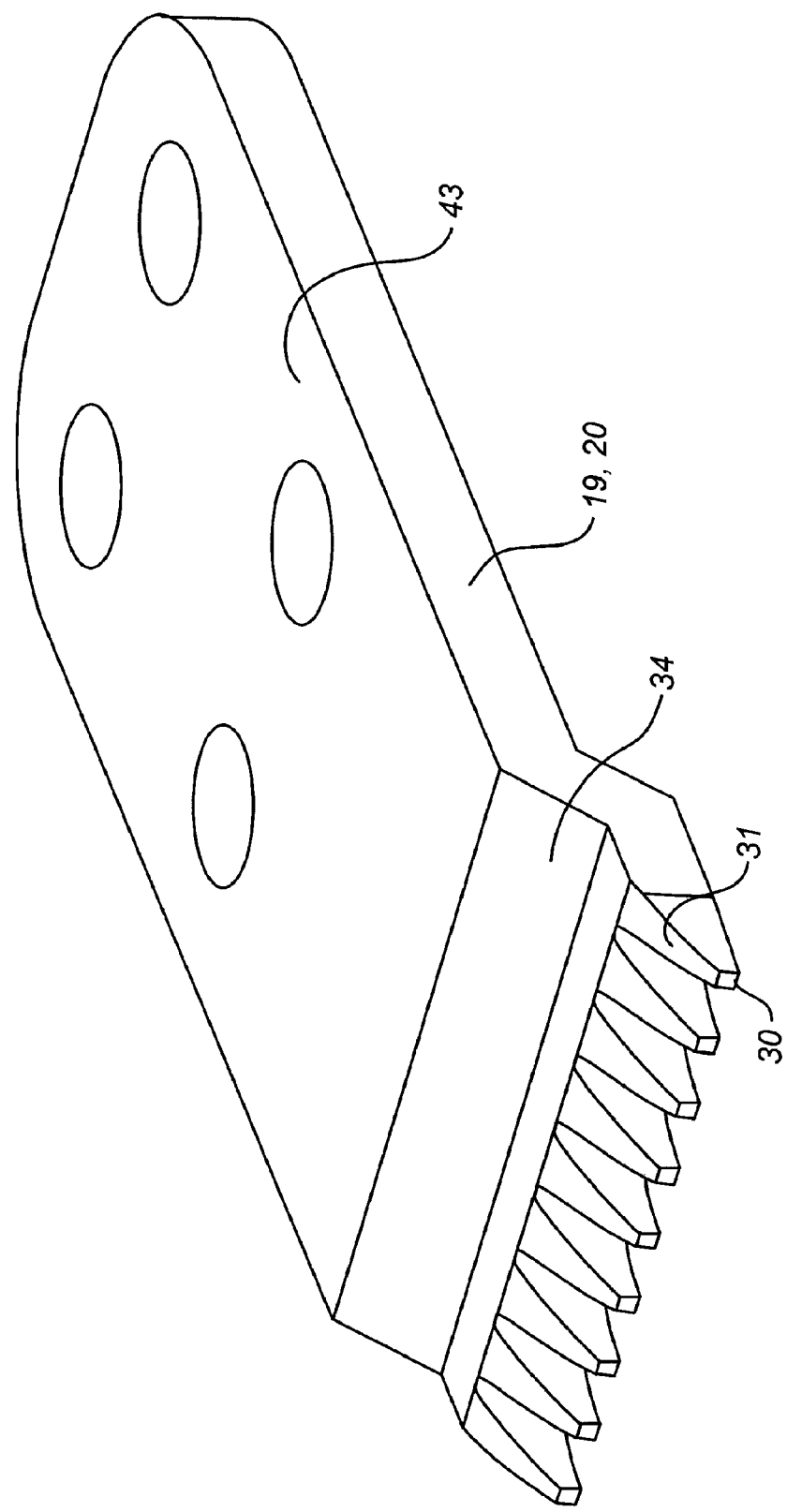
FIG. 10 is an isometric view of an alternative dissecting element or dissecting housing.

FIG. 10 is an isometric view of another configuration of dissecting element 19 or dissector housing 20 that is tapered 31 and features angular surfaces to offset the grooved tooth section from the mounting plane 43. This configuration allows the toothed section to be mated closely with either the complimentary dissecting element or dissecting housing.

An additional aspect is directed to a kit for removing a portion of a lung from structures of the lung. The kits can be configured to comprise any of the devices or components described above with respect to FIGS. 3-10. The kits comprise, for example, a surgical instrument comprising an elongated housing having a longitudinal axis, a forward portion and a rearward portion of the housing, and a dissecting member extending from the forward portion of the housing; and a hole-making instrument for making an entry site to access a target lung section for the surgical instrument. The surgical instrument can be any suitable surgical instrument adapted and configured to remove a portion of a lung from structures of the lung. Additionally, the kit can be configured to include a variety of other components, including, for example, an optical instrument for communicating a visual of a target of the surgical instrument, such as an endoscope, a tensioning device, etc.

In a method embodiment, lobectomy surgery is performed using the invention to make dissections to separate adjacent pleura to complete the fissures between the lobe that is to be removed and adjacent lobes. The method includes the step of locating large airways, arteries and veins larger than approximately 0.5 mm or larger in diameter (e.g. generically referred to as structures) and carefully dissecting out of the lung tissue and/or tumors so they can be reliably clipped, stapled or sealed off with glue or other methods. As will be appreciated by those of skill in the art, failure to identify the critical structures in the lung may result in accidental laceration when the lobe is completely cut away from the adjacent lungs. Laceration or any procedure that allows for rupture of the arteries in this region greatly increases the risk of patient death since they transport the majority of the human cardiac output. Laceration could cause an immediate and uncontrollable hemorrhage that could result in patient death.

An additional method is directed to performing a lobectomy which comprises providing a surgical instrument with a source of work energy that is coupled to a dissecting member extending from the forward portion of the instrument; activating the source to induce motion of the dissecting member; contacting the dissecting member to adjacent pleurae along a fissure; and dissecting a lobe of lung away from a tubular lung structure. Additionally, the method can include visualizing the lung with an optical instrument, such as an endoscope. Tubular lung structure suitable for dissection include, but are not limited to bronchi, dissectible airways, veins and arteries. In some instances it may be desirable to adjust the projection of the dissection member into different trajectories.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. A method of removing a portion of a lung from other portions of the lung, the method comprising:
   providing a surgical instrument with a source of work energy that is coupled to a dissecting member extending at a forward portion of the instrument, the forward portion of the instrument comprising a plurality of grooves having groove widths;
   activating the source to induce a cyclical motion of the dissecting member;
   contacting the forward portion of the instrument to a lung tissue and to a lung structure so that the dissecting member contacts the lung structure, the lung structure comprising an artery, a vein, or an airway having an outer diameter; and
   selectively dissecting lung tissue away from the lung structure with the cyclical motion of the dissecting member while the contact between the lung structure and the forward portion of the instrument inhibits damage to the lung structure, the groove widths being less than the outer diameter of the artery, the vein, or the airway so as to inhibit damage by the cyclical motion of the dissecting member to the artery, the vein, or the airway.

2. The method of claim 1 wherein the instrument is introduced through a hole in the chest wall that is smaller than 10" in diameter.

3. The method of claim 1 wherein the instrument is introduced through a hole in the chest wall that is larger than 10" in diameter.

4. The method of claim 1 wherein the lung tissue is removed while portions of the lung are at least partially inflated with air or blood.

5. The method of claim 1 wherein the instrument is used to dissect while at least one other instrument is employed inside the chest cavity.

6. The method of claim 1 wherein the instrument is used to dissect lung tissue with the benefit of visualization through a scope instrument.

7. The method of claim 1 wherein the instrument is adjusted to project the dissection member into different trajectories.

8. The method of claim 1 further comprising the step of attaching the dissecting member.

9. The method of claim 1 further comprising the step of detaching the dissecting member.

10. The method of claim 9 further comprising the step of replacing the previously detached dissecting member with another functional member.

11. The method of claim 1, wherein the groove widths are less than 3 mm.

12. The method of claim 1, wherein the cyclical motion comprises rotary motion.

13. The method of claim 1, wherein the grooves are defined by teeth that only have sharp edges within the grooves and wherein the groove widths inhibit damage by inhibiting the artery, the vein, or the airway from advancing within the grooves feature.

14. The method of claim 1, wherein edges external to the grooves are dull.

15. The method of claim 1, wherein the grooves are defined by teeth that have faceted tips to reduce the possibility of cutting into a tubular structure in the lung.

16. The method of claim 1, wherein the grooves are adapted to hold the tissue to be selectively dissected from moving to maximize a relative motion between the tissue and the dissecting elements.

17. A method of performing a lobectomy of a lung using a surgical instrument, the method comprising:
   a. providing a surgical instrument with a source of work energy that is coupled to a dissecting member extending at a forward portion of the instrument, the forward portion having a plurality of grooves;
   b. activating the source to induce a reciprocating motion of the dissecting member;
   c. contacting the dissecting member to adjacent pleurae along a fissure; and
   d. dissecting a lobe of lung away from a tubular lung structure with the reciprocating motion of the dissecting member such that the grooves inhibit injury to the tubular lung structure, the tubular lung structure comprising an artery, a vein, or an airway and having an outer diameter, the outer diameter being more than a width of the grooves.

18. The method of claim 17 further comprising visualizing the lung with an optical instrument.

19. The method of claim 17, wherein the surgical instrument is adjusted to project the dissection member into different trajectories.

20. A method of removing a portion of a lung from other portions of the lung, the method comprising:
   providing a surgical instrument with a source of work energy that is coupled to a dissecting member extending at a forward portion of the instrument, the forward portion of the instrument comprising a plurality of grooves having groove widths;
   activating the source to induce a cyclical motion of the dissecting member;
   contacting the forward portion of the instrument to a lung tissue and to a lung structure so that the dissecting member contacts the lung structure, the lung structure comprising a tubular tissue having an outer diameter; and selectively dissecting lung tissue away from the lung structure with the cyclical motion of the dissecting member while the contact between the outer diameter of the lung structure and the groove widths of the forward portion of the instrument inhibits damage to the lung structure;

wherein the cyclical motion comprises a reciprocating motion of the dissection member along a major surface of the dissection member, wherein the dissection member comprises teeth defining the grooves therebetween, and wherein the forward portion of the instrument comprises a grooved body extending along the major surface of the dissection member such that relative motion between teeth of the grooved body and the teeth of the dissection member discriminatingly separates the lung tissue from the lung structure while inhibiting injury to the lung structure, the tubular tissue of the lung structure comprising a vein, an artery, or an airway.

\* \* \* \* \*